United States Patent [19]
Garces et al.

[11] Patent Number: 5,736,161
[45] Date of Patent: Apr. 7, 1998

[54] PHARMACEUTICAL PREPARATION FOR IMPROVING THE BIOAVAILABILITY OF DRUGS WHICH ARE DIFFICULT TO ABSORB AND A PROCEDURE FOR OBTAINING IT

[75] Inventors: Jose de los Santos Garces; Angel Bonilla Muñoz; Jose Maria Garcia Anton, all of Barcelona, Spain

[73] Assignee: Lipotec S.A., Barcelona, Spain

[21] Appl. No.: 278,520

[22] Filed: Jul. 21, 1994

[30] Foreign Application Priority Data

Jul. 21, 1993 [ES] Spain ................................ 9301637

[51] Int. Cl.$^6$ .............................. A61K 9/16; A61K 9/50; A61K 9/54; A61K 9/62
[52] U.S. Cl. .............. 424/493; 424/458; 424/459; 424/461; 424/463; 424/490; 424/498; 514/777; 514/775; 514/780; 514/779; 514/782; 514/784
[58] Field of Search ................................. 424/490, 493, 424/494, 498, 458, 459, 461, 463

[56] References Cited

U.S. PATENT DOCUMENTS 5,215,757  6/1993  El-Nokaly .......................... 424/488

FOREIGN PATENT DOCUMENTS

0 301 777   2/1989   Canada.
WO 92/00732  1/1992  Sweden.
WO 91/06282  5/1991  United Kingdom.

*Primary Examiner*—James M. Spear
*Attorney, Agent, or Firm*—Wigman, Cohen, Leitner & Myers, PC

[57] ABSTRACT

The preparation consists of millispheres, microspheres, nanospheres or array-type particles consisting of a nucleus of a gellable hydrocolloid onto which has been deposited a film of a cationic polysaccharide, and incorporating inside a pharmacologically useful drug. The procedure consists of dissolving, suspending or emulsifying the drug in a solution of the gellable hydrocolloid; adding the resulting mixture to a gelling solution; and suspending the resulting millispheres, microspheres, nanospheres or array-type particles in a solution of the cationic polysaccharide.

32 Claims, 4 Drawing Sheets

MATRIX

COATING

PHARMACEUTICAL PREPARATION FOR IMPROVING THE BIOAVAILABILITY OF DRUGS WHICH ARE DIFFICULT TO ABSORB AND A PROCEDURE FOR OBTAINING IT

The present invention relates to a new method and compositions for improving the absorption of drugs taken by the oral route by means of encapsulation in millispheres of gellable hydrocolloids covered with positively charged polysaccharides.

BACKGROUND OF THE INVENTION

The oral route is preferred when administering drugs to all kinds of patients due to the advantages of this method relative to other routes which are more aggressive and/or more difficult to apply (intravenous, parenteral, subcutaneous ... ). Nevertheless, not all drugs are easily absorbed via the gastrointestinal tract. This absorption depends, among other factors, on the permeability of the gastrointestinal mucous membrane to the drug and on the acidic or enzymatic degratative processes to which the drug is subjected whilst it is inside the gastrointestinal tract. It is therefore clear that any factor which improves the speed of absorption of the drug or protects it from the above mentioned degradative processes will improve the clinical efficiency of that drug.

Recently a considerable amount of effort has been made to identify agents which are able to increase the permeability of the gastrointestinal mucous membrane to poorly absorbed products. Tensioactives (George, Sutter, Finegold, J. Infec. Dis. 136, 822 (1977), chellating agents (Cassidy, Tidball, J. Cell. Biol. 32, 672 (1967), salicylates (Higuchi, et al., U.S. Pat. No. 4,462,991 (1984), anti-inflammatory agents (Yaginuma, et al., Chem. Pharm. Bull. 29 1974 (1961), phenothiazines (Alexander and Fix, U.S. Pat. No. 4,425,357 (1984) acyl carnitines (Alexander and Fix, U.S. Ser. No. 606,054) U.S. Pat. No. 4,537,772, fatty acids (Yamazaki, et al., J. Pharm. Pharmacol., 42, 441, (1990) have been described as able to increase gastrointestinal permeability to a large variety of compounds. Furthermore, considerable efforts have also been made to produce systems which protect drugs from the degradative gastrointestinal processes. Coverings of farinose (WO 89/11269), Polymers of lactic and glycolic acid (EP 0202159) and Calcium alginate (Chong-Kook K., Eun-Jin L., Int. J. Pharm., 79, 11, (1992), have been described as systems for administering drugs by the gastrointestinal route.

PCT WO 87/03197 describes microspheres which are less than 200 μm in size and which are obtained from a drug and a material that has ionic exchange properties, such as diethylaminoethyl-dextran.

PCT WO 88/090163, WO 89/032207, WO 91/02545 and WO 91/06282 describe microspheres which are less than 200 μm in size and whose centres are made of starch, starch derivatives, gelatine, albumen, collagen, dextran or dextran derivatives and which can optionally be covered by polymers such as alginates or diethylaminoethyl-dextrans among others. The use of such microspheres is always described with reference to application by routes other than the oral route and they can optionally be provided with absorption promoters such as lysolecithins or alginates.

EP 391803 describes an industrial procedure for obtaining capsules of alginates in a continuous process by a procedure which is itself described in previous literature (Grant, G. I., et al.; FEBS Lett. 32, 195 (1973).

PCT WO 92/00732 describes pellets of polysaccharides (in particular pectins) which are able to form coacervates with polyvalent cations, containing a drug and covered again by the same type of polysaccharide. These particles are administered by the oral route, the drug being liberated in the colon after the polysaccharide covering has been dissolved by bacteria.

BRIEF DESCRIPTION OF THE INVENTION

The presence of a certain negative charge density on the surface of most gastrointestinal mucous membranes is known, and the authors therefore directed their research towards obtaining a system of administering drugs by the oral route consisting of millispheres with a certain degree of positive surface charge (covered with cationic polysaccharides) in order to achieve a bioadhesive effect on the surface of the gastrointestinal mucous membranes.

As a result of this research it was discovered, surprisingly, that when drugs which are difficult to absorb gastrointestinally are administered by the oral route incorporated inside millicapsules of gellable hydrocolloids reticulated with cationic polysaccharides, there is a marked increase in the bioavailability of said drugs, and that this increase in the bioavailability of the encapsulated drug relative to the bioavailability of the free drug is even greater if promoters of absorption via the mucous membranes are encapsulated together with the drug.

Therefore, one object of the present invention is to improve the bioavailability of drugs which are difficult to absorb when administered by the oral route by means of encapsulating the drugs inside matrices of gellable hydrocolloids whose surfaces are covered by cationic polysaccharides, optionally incorporating together with the drug products which are able to modify the permeability of the gastrointestinal mucous membranes to the drug which is encapsulated.

A further object of the present invention is a new system of administering drugs by the oral route consisting of millispheres, microspheres, nanospheres or array-type particles of salts of gellable hydrocolloids whose surfaces are covered by cationic polysaccharides, and incorporating a pharmacologically active drug.

A further object of the present invention is a new system of administering drugs by the oral route, consisting of millispheres, microspheres, nanospheres or array-type particles of salts of gellable hydrocolloids whose surfaces are covered by cationic polysaccharides, and incorporating a pharmacologically active drug together with one or several promoters of absorption via the mucous membranes.

A further object of the present invention is a new system of administering drugs by the oral route, consisting of millispheres, microspheres, nanospheres or array-type particles of salts of gellable hydrocolloids whose surfaces are covered by cationic polysaccharides, and incorporating a pharmacologically active drug wherein optionally, and in particular in the case of drugs which are sensitive to the chemical/enzymatic conditions of the stomach, said particles are administered inside capsules of gelatine with an enteric covering which protects the particles until they enter the duodenum.

These formulations have the inherent advantages of the oral route compared with other routes for administering drugs, i.e. they are easier to administer, more comfortable, less aggressive and safer for the patient.

Furthermore, the formulations claimed have the advantage of enabling the drugs incorporated to reach the circulatory system without being destroyed during their passage through the digestive tract, in addition providing a high degree of bioavailability of the drug administered.

DETAILED DESCRIPTION OF THE INVENTION

Figure 1:
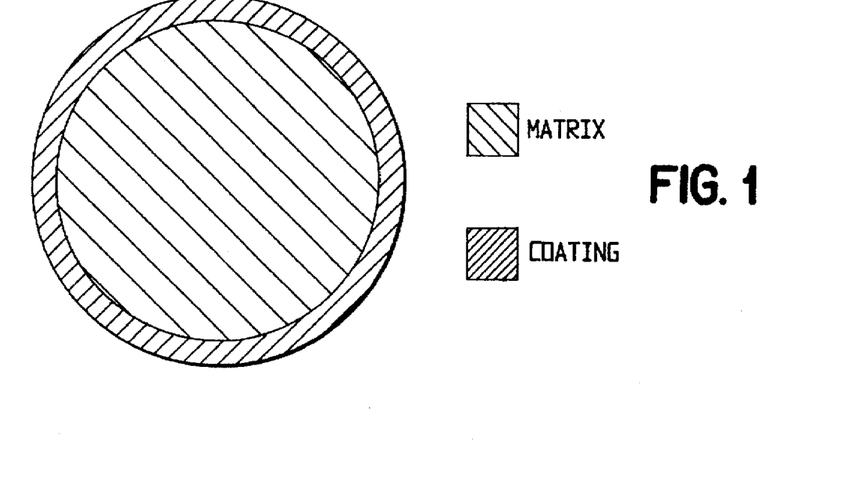
FIG. 1 represents a millisphere consisting of a matrix of a gellable hydrocolloid which contains the drug and onto which has been deposited a covering film of a cationic saccharide, according to the present invention.

The present invention comprises the preparation and use of millispheres, microspheres, nanospheres or array-type particles consisting of a nucleus or matrix of a gellable hydrocolloid onto which has been deposited a film of a cationic polysaccharide, the matrix of gellable hydrocolloid being able to incorporate one or several pharmacologically active drugs, and where optionally it is possible to incorporate together with the drug or drugs one or several promoters of absorption via the mucous membranes.

Figure 2:
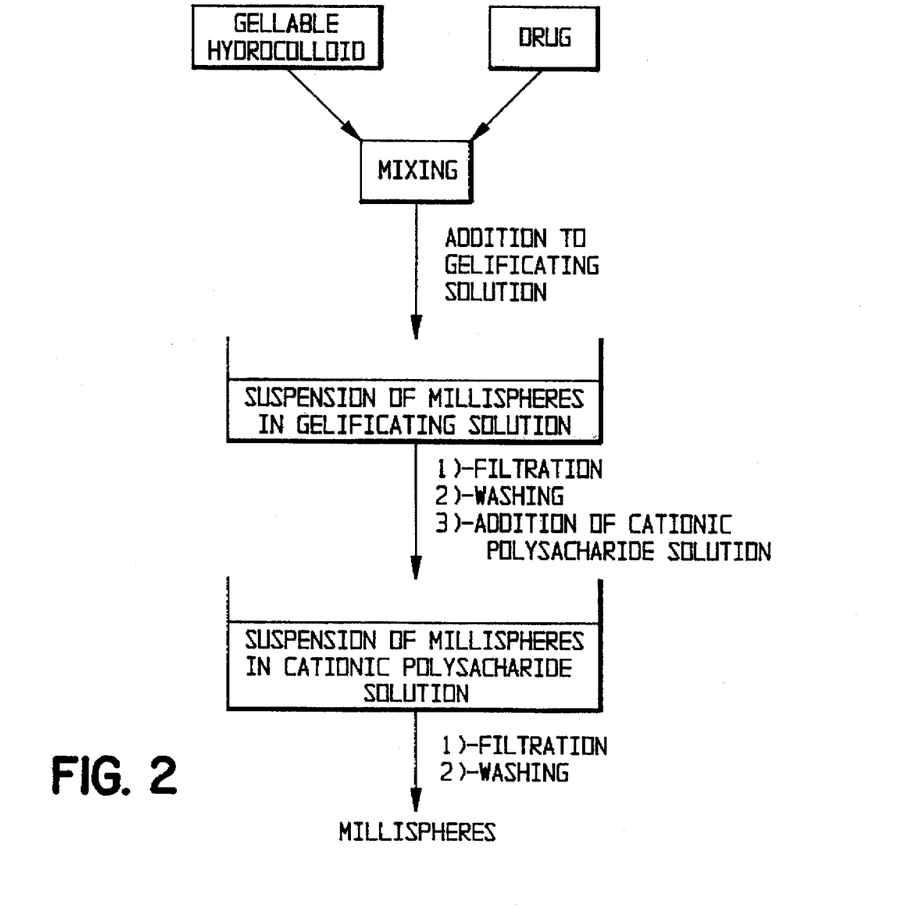
FIGS. 2 and 3 are flow diagrams of the method of incorporating the drug inside the matrix of gellable hydrocolloid by means of dissolving the drug in the solution of the gellable hydrocolloid prior to the gelling thereof.
Figure 3:
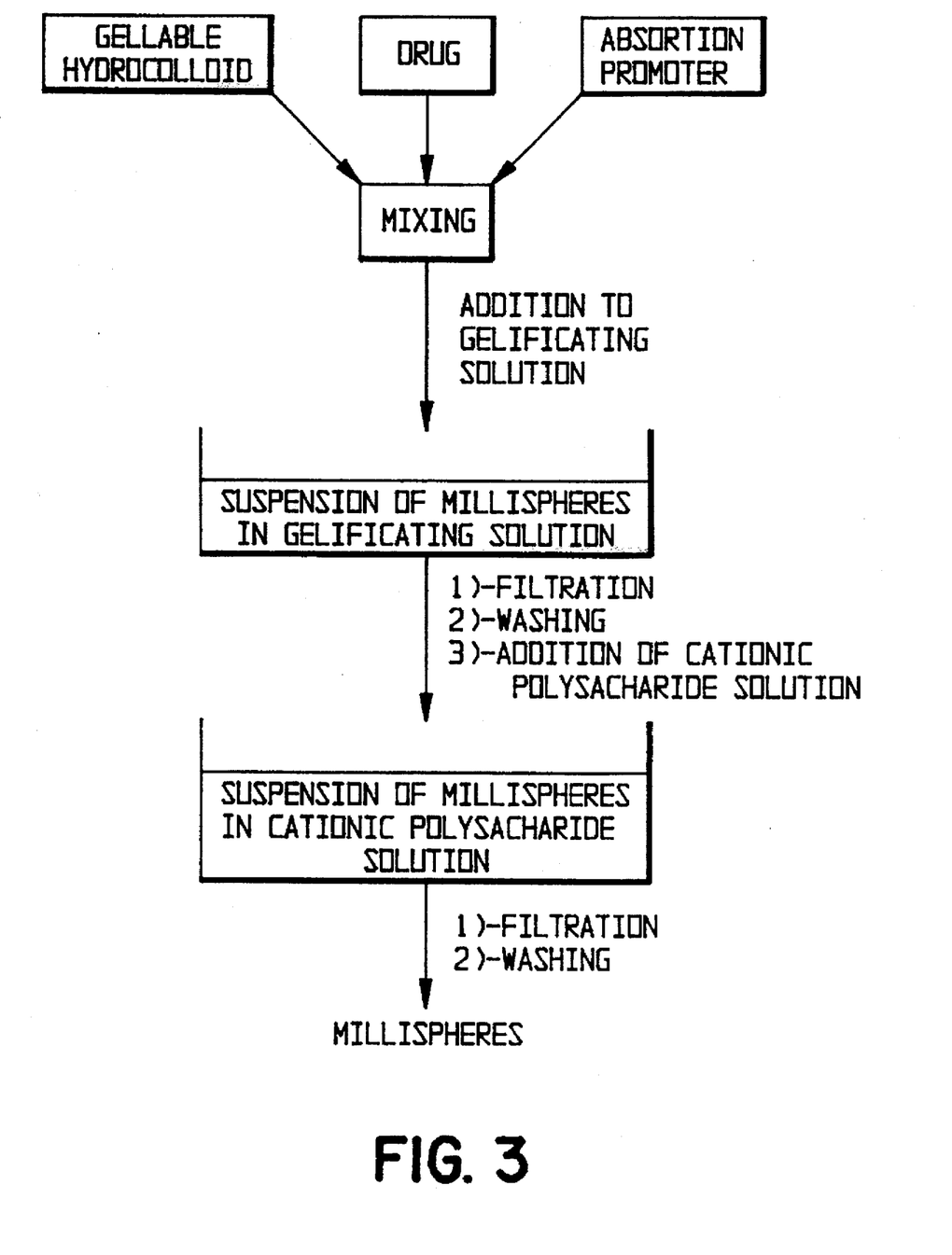

The incorporation of the drug inside the matrix of gellable hydrocolloid can be carried out principally in the following two ways:

1)—The drug is dissolved in the solution of the gellable hydrocolloid prior to the gelling thereof.

Figure 4:
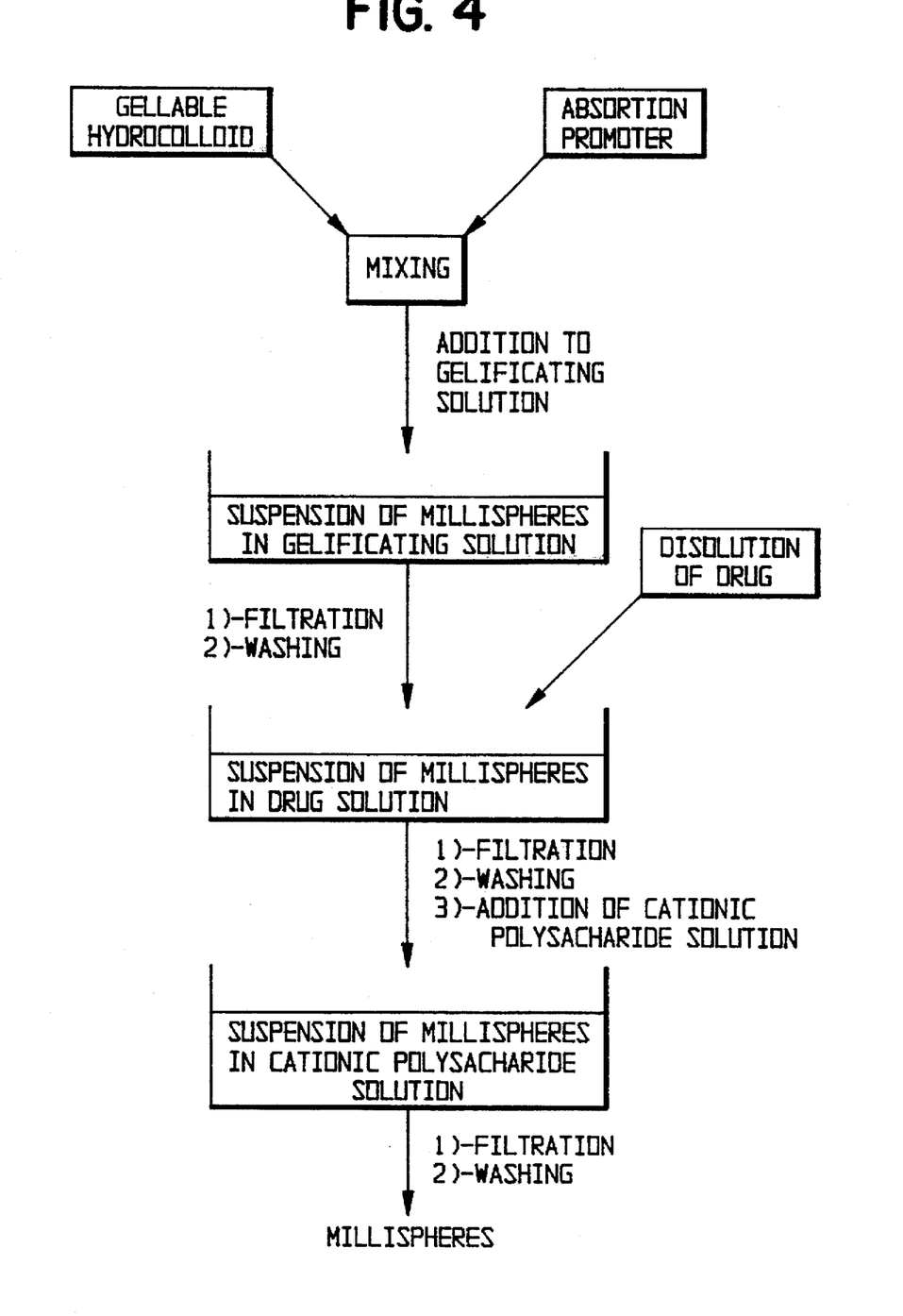
FIGS. 4 and 5 are flow diagrams of the method of incorporating the drug inside the matrix of gellable hydrocolloid by the diffusion of the drug towards the matrix from a concentrated solution of the drug, after the gelling of the matrix and before covering with the cationic polysaccharide.
Figure 5:
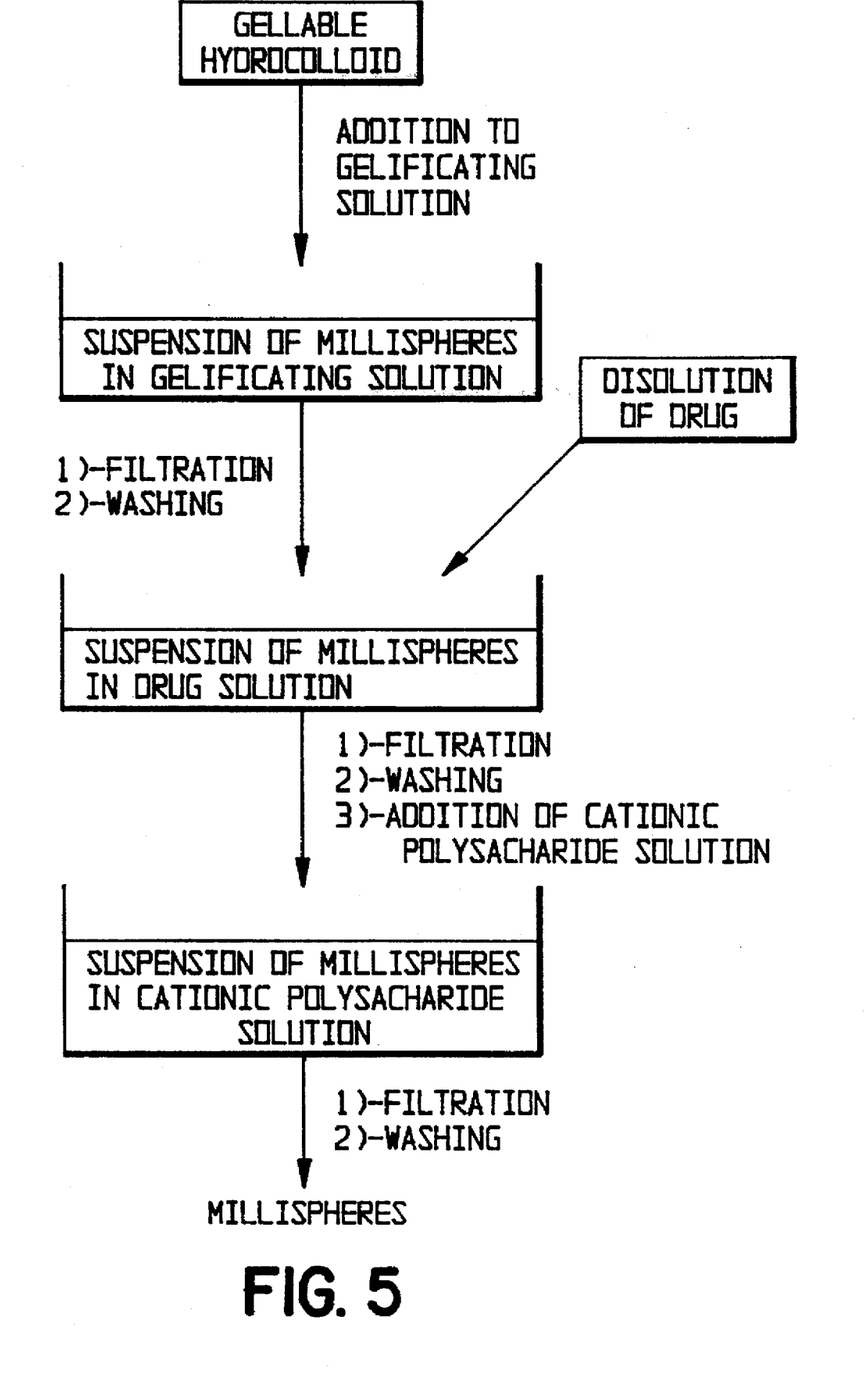

2)—The drug is incorporated by diffusion towards the hydrocolloid matrix from a concentrated solution of the drug, after the gelling of the matrix and before covering with the cationic polysaccharide.

Before continuing with the description of the present invention, reference is made to the accompanying drawings which are included in order that the invention may be better understood. In the drawings.

BRIEF DESCRIPTION OF THE DRAWINGS

Gellable hydrocolloids is taken to refer to all polymers of biological or synthetic origin which are soluble in water and which can form solid gels by the cooling of their aqueous solutions, by interaction with the salts of metallic elements (more particularly the salts of alkaline-earth metals and more particularly calcium salts), by variations in the pH of their aqueous solutions, or by chemical reticulation. More particularly, gellable hydrocolloids is taken to refer to the following biopolymers: agar, pectin, xanthane gum, guar gum, locust bean gum, hyaluronic acid, casein and their mixtures, and even more particularly gellable hydrocolloids is taken to refer to the following biopolymers: water-soluble salts of alginic acid (more particularly sodium alginate), carrageenates and their mixtures.

Cationic polysaccharide is taken to refer to natural polysugars chemically functionalized with residues which can support a positive charge. More particularly cationic polysaccharides is taken to refer to the amino-polysugars and their acid salts, more particularly dextrans functionalized with primary, secondary, tertiary and/or quaternary amine groups, and even more particularly diethylaminoethyl-dextran and dimethylaminoethyl-dextran and their acid salts.

Promoters of absorption via the mucous membranes is taken to refer to all compounds capable of increasing the bioavailability of a drug when administered together with the drug by application to the nasal, gastrointestinal or vaginal mucous membranes or by the transdermic route. More particularly absorption promoters is taken to refer to the following groups of compounds:

—Esters of choline
—Chellating agents
—Salicylates
—Phenothiazines
—Acyl carnitins
—Alpha-cetoaldehydes
—Tensioactives
—Collates
—Lysolecithins More particularly absorption promoters is taken to refer to lysolecithin and to the salts of fatty acids, in particular sodium caproate (sodium hexanoate), sodium caprylate (sodium octanoate), sodium caprate (sodium decanoate) and sodium laurate (sodium dodecanoate).

The drugs which can be incorporated in the new system for administering drugs which forms the object of the present invention include, but are not limited to, the following:

—Anti-bacterial drugs such as gentamycin; quinolones such as ciprofloxacin; penicillins or cephalosporins.

—Anti-viral agents such as rifampicin or acyclovir.

—Anti-fungal compounds such as anphoterecin B, myconazole, terconazole, econazole, isoconazole, thioconazole, biphonazole, clotrimazole, ketoconazole, butaconazole, itraconazole, oxiconazole, phenticonazole, nystatin, naphthyphene, zinoconazole, cyclopyroxolamine or fluconazole.

—Anti-parasitic compounds such as derivatives of antimony.

—Anti-tumoral and anti-neoplastic compounds such as adriamycin, vinblastine, vincristine, mitomycin C, doxorubicin, daunorubicin, methotrexate, cisplatin and others.

—Anti-metabolites.

—Proteins such as albumen.

—Toxins such as diphtheric toxin.

—Enzymes such as catalase.

—Peptides such as hirudin, somatostatin or timopentin.

—Hormones such as oestrogen.

—Peptide hormones such as human growth hormone, porcine growth hormone, bovine growth hormone, human calcitonin, salmon calcitonin, carbocalcitonin, insulin or LHRH and analogues.

—Hormonal antagonists.

—Neurotransmitters such as acetylcholine.

—Neurotransmitter antagonists.

—Glycoproteins such as hyaluronic acid.

—Lipoproteins such as alpha-lipoprotein.

—Immunoglobulins such as IgG.

—Immunomodulators such as interferon or interleukin.

—Immunosuppressors such as cyclosporin-A.

—Vasodilators.

—Colourings such as Arsenaze III.

—Radioactive labellers such as $^{14}C$.

—Radio-opaque compounds such as $^{90}$Te.

—Fluorescent compounds such as carboxy-fluorescein.

—Cellular receptors such as oestrogen receptor protein.

—Non-steroidal anti-inflammatory agents such as indomethacin, ibuprofen, sulindac, diclofenac, ketorolac or naproxen.

—Anti-inflammatory agents such as dexamethasone.

—Anti-glaucomatous agents such as pilocarpine or thymolol.

—Mydriatic compounds.

—Local anaesthetics such as lidocaine.

—Narcotics such as codeine.

—Vitamins such as alpha-tocopherol.

—Nucleic acids such as thymine.

—Polynucleotides such as RNA.

—Psychoactive or anxiolytic compounds such as diazepam.

—Mono-, di- and poly-saccharides such as glycogen.

—Glycosaminoglycanes such as non-fractionated heparins, heparins of low molecular weight, pentasaccharide, dermatan sulphate and its derivatives, heparan sulphate and its derivatives, chondroitin-4-sulphate or chondroitin-6-sulphate and its derivatives.

—Cardiovascular agents such as alpha-blockers, beta-blockers, calcium channel blockers, ACE inhibitors, histamine H2 receptor inhibitors or serotonin H3T receptor inhibitors.

—Prostaglandins.

Optionally, and in particular in the case of drugs which are sensitive to the chemical/enzymatic conditions of the stomach, said particles are administered inside capsules of gelatine with an enteric covering which protects the particles until they enter the duodenum.

The invention is illustrated below by means of the following non-limiting examples of the scope of said invention.

EXAMPLE 1

Obtaining capsules of calcium alginate covered with DEAE-Dextran incorporating sodium heparin of low molecular weight (SLMWH).

500 mg of SLMWH (4 kDaltons) are dissolved in 10 ml of 1% sodium alginate solution by shaking gently. The resulting solution is added drop by drop through a 0.8 mm hole to 40 ml of a gently shaken 0.25M solution of $CaCl_2$ in $H_2O$. Once the addition of the millispheres is complete they are kept in the bulk of the shaken $CaCl_2$ solution for 10 minutes, after which time the balls are separated by filtering and washed with 25 ml of deionized $H_2O$.

The spheres of calcium alginate thus formed are re-suspended in 20 ml of an 8% solution of diethylaminoethyl-dextran hydrochloride (Mr=500000) in $H_2O$, keeping the system gently shaken for 30 minutes.

The spheres are separated by filtering, washed twice with 20 ml of deionized $H_2O$ and dried.

EXAMPLE 2

Obtaining capsules of calcium alginate covered with DEAE-dextran incorporating sodium heparin of low molecular weight (SLMWH) and sodium caprate.

500 mg of SLMWH (4 kDaltons) and 200 mg of sodium caprate are dissolved in 10 ml of 1% sodium alginate solution by shaking gently. The resulting solution is added drop by drop through a 0.8 mm hole to 40 ml of a gently shaken 0.25M solution of $CaCl_2$ in $H_2O$. Once the addition of the millispheres is complete they are kept in the bulk of the shaken $CaCl_2$ solution for 10 minutes, after which time the balls are separated by filtering and washed with 25 ml of deionized $H_2O$.

The spheres of calcium alginate thus formed are re-suspended in 20 ml of an 8% solution of diethylaminoethyl-dextran hydrochloride (Mr=500000) in $H_2O$, keeping the system gently shaken for 30 minutes.

The spheres are separated by filtering, washed twice with 20 ml of deionized $H_2O$ and dried.

EXAMPLE 3

Obtaining capsules of calcium alginate covered with DEAE-Dextran incorporating sodium heparin of low molecular weight (SLMWH). Method of encapsulation by diffusion.

10 ml of 1% sodium alginate solution are added through a 0.8 mm hole to 40 ml of a 0.25M solution of $CaCl_2$. The system is kept shaken for 10 minutes.

The spheres formed are separated by filtering and washed with 25 ml of deionized $H_2O$, after which they are re-suspended in a solution of heparin, with a concentration of 100 mg/ml, and kept in the bulk of said solution and gently shaken for a period of 6 hours to allow the drug to diffuse inside the capsules. The capsules are then separated by filtering and washed three times with 25 ml of $H_2O$.

The spheres of calcium alginate incorporating SLMWH thus formed are re-suspended in 20 ml of an 8% solution of diethylaminoethyl-dextran hydrochloride (Mr=500000) in $H_2O$, keeping the system gently shaken for 30 minutes.

The spheres are separated by filtering, washed twice with 20 ml of deionized $H_2O$ and dried.

EXAMPLE 4

Obtaining capsules of calcium alginate covered with DEAE-Dextran incorporating sodium heparin of low molecular weight (SLMWH) and sodium caprate. Method of encapsulation by diffusion.

10 ml of 1% sodium alginate solution containing 2% sodium caprate are added through a 0.8 mm hole to 40 ml of a 0.25M solution of $CaCl_2$. The system is kept shaken for 10 minutes.

The spheres formed are separated by filtering and washed with 25 ml of deionized water, after which they are re-suspended in a solution of heparin, with a concentration of 150 mg/ml, and kept in the bulk of said solution and gently shaken for a period of 6 hours to allow the drug to diffuse inside the capsules. The capsules are then separated by filtering and washed three times with 25 ml of $H_2O$.

The spheres of calcium alginate incorporating SLMWH thus formed are re-suspended in 20 ml of an 8% solution of diethylaminoethyl-dextran hydrochloride (Mr=500000) in $H_2O$, keeping the system gently shaken for 30 minutes.

The spheres are separated by filtering, washed twice with 20 ml of deionized $H_2O$ and dried.

EXAMPLE 5

Bioavailability tests on the capsules prepared according to examples 1 and 2.

—Design:

Bioavailability studies in which the animals received 40 mg of heparin by the oral route or 10 mg by the subcutaneous route over a period of three days.

—Animals:

Four dogs (2 for each treatment), each approximately 15 kg in weight.

—Measurements:

A bioassay (anti-Xa activity) was used to measure the concentrations in the plasma.

EXAMPLE 6

Incorporation procedures for several drugs

| DRUG | GELLABLE HYDROCOLLOID | CATIONIC POLYSACCHARIDE | ABSORPTION PROMOTER | METHOD OF INCORPORATING THE DRUG |
|---|---|---|---|---|
| ACYCLOVIR | Sodium alginate | DEAE-Dextran | Lysolecithin | Example No 2 |
| ACYCLOVIR HYDROCHLORIDE | Carrageenate | DEAE-Dextran | | Example No 3 |
| CYCLOSPORIN | Sodium alginate | DEAE-Dextran | Sodium caprate | Example No 2 |
| CYCLOSPORIN | Sodium alginate | DEAE-Dextran | | Example No 1 |
| CALCITONIN | Sodium alginate | DEAE-Dextran | Lysolecithin | Example No 2 |
| CARBOCALCITONIN | Sodium alginate | DEAE-Dextran | Sodium caprate | Example No 2 |
| INSULIN | Sodium alginate | DEAE-Dextran | Sodium caprate | Example No 2 |
| ERYTHROMYCIN | Sodium alginate | DEAE-Dextran | Sodium caprate | Example No 1 |
| NIMODIPIN | Sodium alginate | DEAE-Dextran | | Example No 2 |
| FLUCONAZOLE | Sodium alginate | DEAE-Dextran | Sodium caprate | Example No 2 |
| CIPROFLOXACIN | Sodium alginate | DEAE-Dextran | Sodium caprate | Example No 4 |
| FAMOTIDIN | Sodium alginate | DEAE-Dextran | Sodium caprate | Example No 2 |
| KETOROLAC THROMETAMIN | Sodium alginate | DEAE-Dextran | Lysolecithin | Example No 4 |
| DICLOFENAC | Sodium alginate | DEAE-Dextran | | Example No 2 |

The anti-Xa activity in the plasma was measured ex-vivo using a chromogenic test using a commercially available kit (Coatest) and expressed in IU/ml. The values were calculated from a calibration curve obtained in-vitro by adding different quantities of SLMWH to dog plasma.

The blood was extracted from the femoral vein. Starting on the second day of experiments samples were collected before and 1, 2, 3, 4 and 6 hours after oral or subcutaneous administration, sodium citrate was added to the samples (9 vol. sangre:1 vol. 3.8% sodium citrate) followed by centrifuging at 1200 rpm for 20 minutes at 4° C. The plasma was separated immediately and the anti-Xa activity was tested.

The urine samples were treated with chondroitinase AC to eliminate the endogenous chondroitins. The residue was analyzed by means of proton NMR and HPLC (to determine the molecular weight).

—Results:

Even on the second day of experiments, the levels of heparin in the blood as a result of administering SLMWH in the form of capsules by the oral route, or injected subcutaneously, were detectable using the anti-Xa activity method.

Comparable peak values (0.2–0.4 IU/ml) were found after subcutaneous or oral administration, as well as a significant continued activity (>0.1 IU/ml) for 3 hours only after subcutaneous administration.

On the third day of experiments the basal values of anti-Xa activity before the final dose were significantly higher than the corresponding values on the previous day.

Peak values (0.8–1.2 IU/ml) were found 1 and 2 hours after oral and subcutaneous administration as well as a significant activity (>0.3 IU/ml) after 6 hours in the case of both treatments.

The urine analyses gave the following results:

The $H_1$-NMR test detected the presence of partially disulphated heparin.

The HPLC test indicated a molecular weight of 5 kDaltons.

We claim:

1. A pharmaceutical preparation, comprising microparticles selected from the group consisting of dehydrated millispheres, dehydrated microspheres, dehydrated nanospheres and dehydrated particles, said microparticles comprising hydrocolloid onto which has been deposited a film of a cationic polysaccharide, a promoter of adsorption via the mucous membranes and incorporating within the hydrocolloid of the microparticle a pharmacologically useful drug.

2. A pharmaceutical preparation comprising:

a pharmaceutically useful drug;

a water soluble, gellable hydrocolloid formed into particles, said drug being dissolved or suspended within said particles;

said particles being coated with a film of a cationic polysaccharide to form a coated particle;

said coated particle being dried to form a dehydrated coated particle.

3. A pharmaceutical preparation according to claim 1, wherein the gellable hydrocolloids are polymers of biological or synthetic origin which are soluble in water and which can form solid gels by the interaction with the salts of metallic elements or by variations in the pH of their aqueous solutions or by chemical reticulation.

4. A pharmaceutical preparation according to claim 3, wherein the gellable hydrocolloids are selected from the group consisting of agar, pectin, xanthan gum, guar gum, locust bean gum, hyaluronic acid, casein, water-soluble salts of alginic acid, sodium alginate and mixtures thereof.

5. A pharmaceutical preparation according to claim 1, wherein the cationic polysaccharides are natural polysugars with residues which can support a positive charge and natural polysugars chemically functionalized with residues which can support a positive charge.

6. A pharmaceutical preparation according to claim 1, wherein the drugs incorporated are:

anti-bacterial drugs, anti-viral agents, anti-fungal compounds, anti-parasitic compounds, anti-tumoral and anti-neoplastic compounds, anti-metabolites, proteins, toxins, enzymes, peptides, hormones, peptide hormones, hormonal antagonists, neurotransmitters, neurotransmitter antagonists; glycoproteins, lypoproteins, immunoglobulines, immunomodulators, immunosuppressors, vasodilators, colorings, radioactive labelers, radio-opaque compounds, fluorescent compounds, cellular receptors, non-steroidal anti-inflammatory agents, anti-inflammatory agents, anti-glaucoma agents mydriatic compounds, local anaesthetics, narcotics, vitamins, nucleic acids, polynucleotides, psychoactive or anxiolytic compounds, mono-, di- and polysaccharide, cardiovascular agents and prostaglandins.

7. A pharmaceutical preparation according to claim 1, wherein the promoters of absorption via the mucous membranes are selected from the group consisting of choline esters, chelating agents, salicylates, phenothiazines, acyl carnitines, alpha-cetoaldehydes, tensioactives, cholates, lysolecithins and mixtures thereof.

8. A pharmaceutical preparation according to claim 7, wherein the promoters of absorption via the mucous membranes are lysolecithin and salts of fatty acids, the fatty acids being selected from the group consisting of, hexanoic acid, octanoic acid, decanoic acid and dodecanoic acid and mixtures thereof.

9. A pharmaceutical preparation according to claim 6, wherein the drugs incorporated are:

anti-bacterial drugs selected from the group consisting of gentamycin, quinolones penicillins or cephalosporins;

anti-viral agents selected from the group consisting of rifampicin or acyclovir;

anti-fungal compounds selected from the group consisting of amphoterecin B, myconazole, terconazole, econazole, isoconazole, thioconazole, biphonazole, clotrimazole, ketoconazole, butaconazole, itraconazole, oxiconazole, phenticonazole, nystatin, naphthyphene, zinoconazole, cyclopyroxolamine or fluconazole;

anti-parasitic compounds selected from the group of antimony anti-parasitic compounds;

anti-tumoral and anti-neoplastic compounds selected from the group consisting of adriamycin, vinblastine, vincristine, mitomycin C, doxorubicin, daunorubicin, methotrexate, and cisplatin;

anti-metabolites;

albumen;

diphtheria toxin;

catalase;

peptides selected from the group consisting of hirudin, somatostatin or timopentin;

estrogen;

peptide hormones selected from the group consisting of human growth hormone, porcine growth hormone, bovine growth hormone, human calcitonin, salmon calcitonin, carbocalcitonin, insulin or LHRH;

acetylcholine;

hyaluronic acid;

alpha-lipoprotein;

IgG;

immunomodulators selected from interferon or interleukins;

cyclosporin-A;

Arsenaze III;

$^{14}$C radioactive labelers;

$^{90}$Te radio-opaque compounds;

carboxy-fluorescein;

estrogen receptor protein;

non-steroidal anti-inflammatory agents selected from the group consisting of indomethacin, ibuprofen, sulindac, diclofenac, ketorolac and naproxen;

dexametasone;

anti-glaucoma agents selected from pilocarpine or thymolol;

lidocaine;

codeine;

alpha-tocopherol;

thymine;

RNA;

diazepam;

mono-, di- and poly-saccharide selected from the group consisting of glycogen; heparins, heparins of low molecular weight, pentasaccharide, dermatan sulphate, heparin sulphate, chondroitin-4-sulphate and chondroitin-6-sulphate and mixtures thereof;

cardiovascular agents selected from the group consisting of alpha-blockers, beta-blockers, calcium channel blockers, ACE inhibitors, histamine H2 receptor inhibitors or serotonin H3T receptor inhibitors; and prostaglandins.

10. A procedure for obtaining the pharmaceutical preparation according to claim 1, wherein the drug is dissolved, suspended or emulsified in a solution of a hydrocolloid; the resulting solution, suspension or emulsion is added to a medium in which the gelling of the hydrocolloid takes place; the microparticles which are formed are separated and suspended in a solution of the cationic polysaccharide where the deposition of the cationic polysaccharide onto the surface of the microparticle takes place, after which the covered microparticles are separated, washed and dried.

11. A procedure for obtaining the pharmaceutical preparation according to claim 1, wherein the drug and the absorption promoter are dissolved, suspended or emulsified in a solution of the hydrocolloid solution; the resulting solution, suspension or emulsion is added to a medium in which the gelling of the hydrocolloid takes place; the microparticles which are formed are separated and suspended in a solution of the cationic polysaccharide where the deposition of the cationic polysaccharide onto the surface of the microparticles takes place, after which the covered microparticles are separated, washed and dried.

12. A procedure for obtaining the pharmaceutical preparation according to claim 1, wherein the absorption promoter is dissolved, suspended or emulsified in a solution of the hydrocolloid; the resulting solution, suspension or emulsion is added to a medium in which the gelling of the hydrocolloid takes place; the microparticles which are formed are separated and suspended in a concentrated solution of the drug from which the drug diffuses inside the microparticles; then the microparticles are separated and suspended in a solution of the cationic polysaccharide where the deposition of the cationic polysaccharide onto the surface of the microparticle takes place, after which the covered microparticles are separated, washed and dried.

13. A procedure for obtaining the pharmaceutical preparation according to claim 1, wherein the solution of the hydrocolloid is added to a medium in which the gelling of the hydrocolloid takes place; the microparticles which are formed are separated and suspended in a concentrated solution of the drug and absorption promoter from which the drug and absorption promoter diffuses inside the microparticles; then the microparticles are separated and suspended in a solution of the cationic polysaccharide where the deposition of the cationic polysaccharide onto the surface of the microparticles takes place, after which the covered microparticles are separated, washed and dried.

14. A pharmaceutical preparation according to claim 1, wherein, said particles are administered inside capsules of gelatine with an enteric covering which protects the particles until they enter the duodenum.

15. The pharmaceutical preparation of claim 3, wherein the salts of metallic elements is the salt of an alkaline earth metal.

16. The pharmaceutical preparation of claim 15, wherein the salt of the alkaline earth metal is a calcium salt.

17. The pharmaceutical preparation of claim 5, wherein the cationic polysaccharides are amino polysugars.

18. The pharmaceutical preparation of claim 5, wherein the cationic polysaccharides are dextran functionalized with primary, secondary, tertiary or quaternary amine groups, their acid salts and mixtures thereof.

19. A pharmaceutical preparation according to claim 18 wherein the cationic polysaccharides are selected from the group consisting of diethylaminoethyl-dextran and dimethylaminoethyl-dextran, their acid salts and mixtures thereof.

20. The pharmaceutical preparation of claim 2, wherein the gellable hydrocolloids are polymers of biological or synthetic origin which are soluble in water and which can form solid gels by the interaction with the salts of metallic elements or by variations in the pH of the aqueous solutions or by chemical reticulation.

21. The pharmaceutical preparation of claim 20, wherein the salts of metallic elements is the salt of an alkaline earth metal.

22. The pharmaceutical preparation of claim 21, wherein the salt of the alkaline earth metal is a calcium salt.

23. The pharmaceutical preparation of claim 20, wherein the gellable hydrocolloids are selected from the group consisting of agar, pectin, xanthan gum, guar gum, locust bean gum, hyaluronic acid, casein, water-soluble salts of alginic acid, sodium alginate and mixtures thereof.

24. The pharmaceutical preparation of claim 2, wherein the cationic polysaccharides are natural polysugars with residues which can support a positive charge and natural polysugars chemically functionalized with residues which can support a positive charge.

25. The pharmaceutical preparation of claim 24, wherein the cationic polysaccharides are dextran functionalized with primary, secondary, tertiary or quaternary amine groups, their acid salts and mixtures thereof.

26. A pharmaceutical preparation of claim 25, wherein the cationic polysaccharides are selected from the group consisting of diethylaminoethyl-dextran and dimethylaminoethyl-dextran, their acid salts and mixtures thereof.

27. The pharmaceutical preparation of claim 2 additionally including promoters of absorption, wherein the promoters of absorption are selected from the group consisting of choline esters, chelating agents, salicylates, phenothiazines, acyl carnitines, alpha-cetoaldehydes, tensioactives, cholates, lysolecithins and mixtures thereof.

28. The pharmaceutical preparation of claim 9, wherein the promoters of absorption via the mucous membranes are lysolecithin and salts of fatty acids, the fatty acids being selected from the group consisting of, hexanoic acid, octanoic acid, decanoic acid and dodecanoic acid and mixtures thereof.

29. A pharmaceutical preparation according to claim 2, wherein the drugs incorporated are:

anti-bacterial drugs;
anti-viral agents;
anti-fungal compounds;
anti-parasitic compounds;
anti-tumoral and anti-neoplastic compounds;
anti-metabolites;
proteins;
toxins;
enzymes;
peptides;
hormones;
peptide hormones;
hormonal antagonists;
neurotransmitters;
neurotransmitter antagonists;
glycoproteins;
lypoproteins;
immunoglobulines;
immunomodulators;
immunosuppressors;
vasodilators;
colorings;
radioactive labelers;
radio-opaque compounds;
fluorescent compounds;
cellular receptors;
non-steroidal anti-inflammatory agents;
anti-inflammatory agents;
anti-glaucoma agents;
mydriatic compounds;
local anaesthetics;
narcotics;
vitamins;
nucleic acids;
polynucleotides;
psychoactive or anxiolytic compounds;
mono-, di- and poly-saccharide;
cardiovascular agents; and
prostaglandins.

30. A method of obtaining the pharmaceutical preparation of claim 2, wherein the drug is placed in a solution of the gellable hydrocolloid, the gellable hydrocolloid solution and drug are then placed in a hydrocolloid gelling solution and the gellable hydrocolloid is allowed to gel; the particles are then separated and suspended in a solution of cationic polysaccharide allowing the deposition of cationic polysaccharide onto the surface of the particles, after which the covered particles are separated, washed and dried.

31. A method of forming the pharmaceutical preparation of claim 2, wherein the solution of the gellable hydrocolloid is added to a medium in which the gelling of the hydrocolloid takes place; the particles which are formed are separated and suspended in a concentrated solution of the drug from which the drug diffuse inside the spheres; then the particles are separated and suspended in a solution of the cationic polysaccharide where the deposition of the cationic polysaccharide onto the surface of the particles takes place, after which the covered particles are separated, washed and dried.

32. A pharmaceutical preparation according to claim 2, wherein the drugs incorporated are:

- anti-bacterial drugs selected from the group consisting of gentamycin, quinolones; penicillins or cephalosporins;
- anti-viral agents selected from the group consisting of rifampicin or acyclovir;
- anti-fungal compounds selected from the group consisting of anphoterecin B, myconazole, terconazole, econazole, isoconazole, thioconazole, biphonazole, clotrimazole, ketoconazole, butaconazole, itraconazole, oxiconazole, phenticonazole, nystatin, naphthyphene, zinoconazole, cyclopyroxolamine or fluconazole;
- anti-parasitic compounds selected from the group of anti-mony anti-parasitic compounds;
- anti-tumoral and anti-neoplastic compounds selected from the group consisting of adriamycin, vinblastine, vincristine, mitomycin C, doxorubicin, daunorubicin, methotrexate, and cisplatin;
- albumen;
- diphtheria toxin;
- catalase;
- peptides selected from the group consisting of hirudin, somatostatin or timopentin;
- estrogen;
- peptide hormones selected from the group consisting of human growth hormone, porcine growth hormone, bovine growth hormone, human calcitonin, salmon calcitonin, carbocalcitonin, insulin or LHRH;
- acetylcholine;
- hyaluronic acid;
- alpha-lipoprotein;
- IgG;
- immunomodulators selected from interferon or interleukins;
- cyclosporin-A;
- Arsenaze III;
- $^{14}C$ radioactive labelers;
- $^{90}Te$ radio-opaque compounds;
- carboxy-fluorescein;
- estrogen receptor protein;
- non-steroidal anti-inflammatory agents selected from the group consisting of indomethacin, ibuprofen, sulindac, diclofenac, ketorolac and naproxen;
- dexamethasone;
- anti-glaucoma agents selected from pilocarpine or thymolol;
- lidocaine;
- codeine;
- alpha-tocopherol;
- thymine;
- RNA;
- diazepam;
- mono-, di- and poly-saccharide selected from the group consisting of glycogen; heparins, heparins of low molecular weight, pentasaccharide, dermatan sulphate, heparin sulphate, chondroitin-4-sulphate and chondroitin-6-sulphate and mixtures thereof;
- cardiovascular agents selected from the group consisting of alpha-blockers, beta-blockers, calcium channel blockers, ACE inhibitors, histamine H2 receptor inhibitors or serotonin H3T receptor inhibitors; and prostaglandins.

* * * * *